United States Patent
Brown et al.

(10) Patent No.: US 6,997,344 B2
(45) Date of Patent: Feb. 14, 2006

(54) AUTOMATED MECHANICAL MECHANISM FOR A BLOOD GLUCOSE SENSOR DISPENSING INSTRUMENT

(75) Inventors: Michael K. Brown, Elkhart, IN (US); Russell J. Micinski, South Bend, IN (US); Robert C. Whitson, Elkhart, IN (US); Norman S. Miller, Elkhart, IN (US)

(73) Assignee: Bayer HealthCare LLC

( * ) Notice: Subject to any disclaimer, the term of this patent is extended or adjusted under 35 U.S.C. 154(b) by 297 days.

(21) Appl. No.: 10/269,484

(22) Filed: Oct. 15, 2002

(65) Prior Publication Data

US 2004/0069793 A1 Apr. 15, 2004

Related U.S. Application Data

(60) Provisional application No. 60/311,759, filed on Aug. 13, 2001.

(51) Int. Cl.
*B65G 59/00* (2006.01)

(52) U.S. Cl. .............................. 221/258; 221/25; 436/44
(58) Field of Classification Search ............. 221/30–31, 221/13, 15, 87–88, 76, 79, 25, 258; 422/61, 422/63, 104, 64; 436/43–44, 46
See application file for complete search history.

(56) References Cited

U.S. PATENT DOCUMENTS

| | | | |
|---|---|---|---|
| 5,489,414 A | | 2/1996 | Schreiber et al. |
| 5,510,266 A | | 4/1996 | Bonner et al. |
| 5,575,403 A | * | 11/1996 | Charlton et al. ............... 221/31 |
| 5,630,986 A | * | 5/1997 | Charlton et al. ............... 422/64 |
| 5,854,074 A | * | 12/1998 | Charlton et al. ............... 436/46 |
| 6,093,156 A | * | 7/2000 | Cunningham et al. ...... 600/573 |
| 6,206,841 B1 | * | 3/2001 | Cunningham et al. ...... 600/584 |
| 6,574,165 B1 | * | 6/2003 | Sharma et al. ................. 368/10 |
| 6,582,962 B1 | * | 6/2003 | Richards et al. ............... 436/46 |
| 6,635,167 B1 | * | 10/2003 | Batman et al. ............. 205/775 |
| 6,770,447 B1 | * | 8/2004 | Maynard et al. ............. 435/7.1 |

FOREIGN PATENT DOCUMENTS

WO    WO 01/23885 A1    4/2001

* cited by examiner

*Primary Examiner*—Richard Ridley
(74) *Attorney, Agent, or Firm*—Alice A. Brewer; Andrew L. Klewitter

(57) ABSTRACT

A sensor dispensing instrument adapted to handle a sensor pack containing a plurality of sensors and to perform a test using one of the sensors. The sensor dispensing instrument includes an outer housing and a disk drive mechanism contained therein for rotating the sensor pack and ejecting one of the sensors from the sensor pack and through a sensor opening on the housing. The disk drive mechanism of the sensor dispensing instrument is operated by pressing a button which activates a motor. The motor moves a disk drive pusher in a first direction to rotate the sensor pack, and then moves the disk drive pusher in a second direction to eject a sensor from the sensor cavity and through the sensor opening.

15 Claims, 10 Drawing Sheets

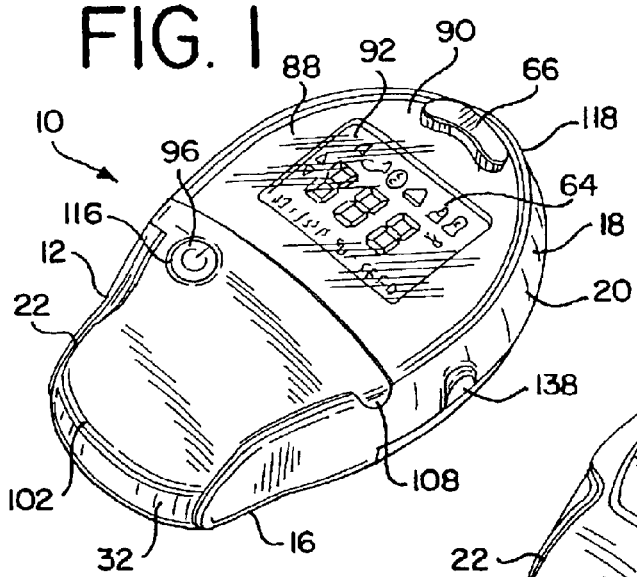
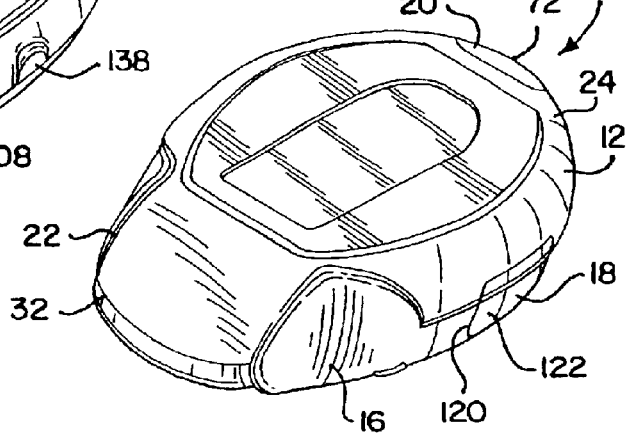
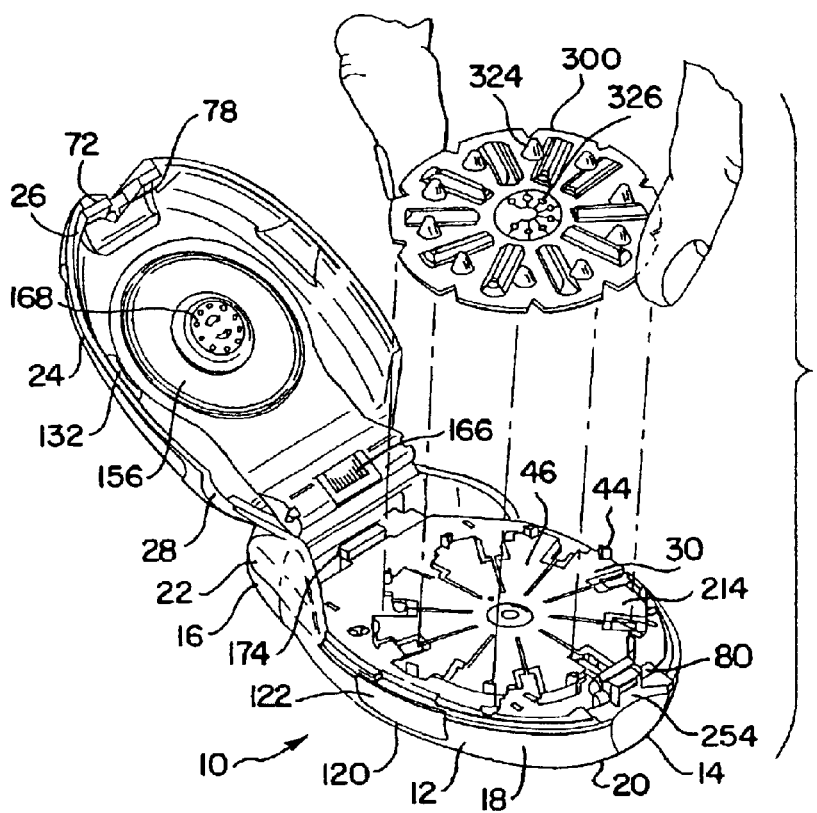

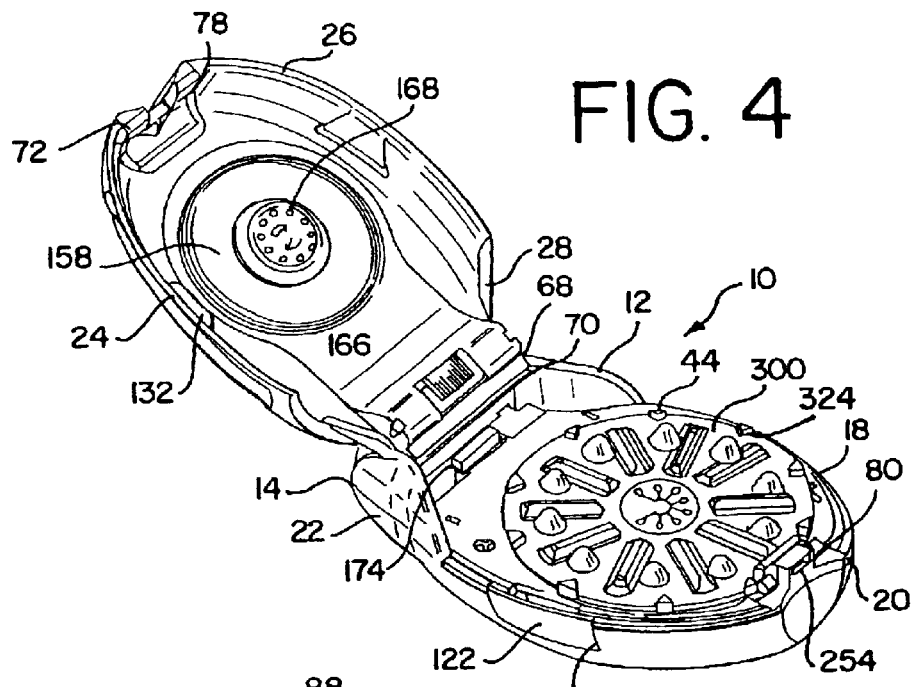
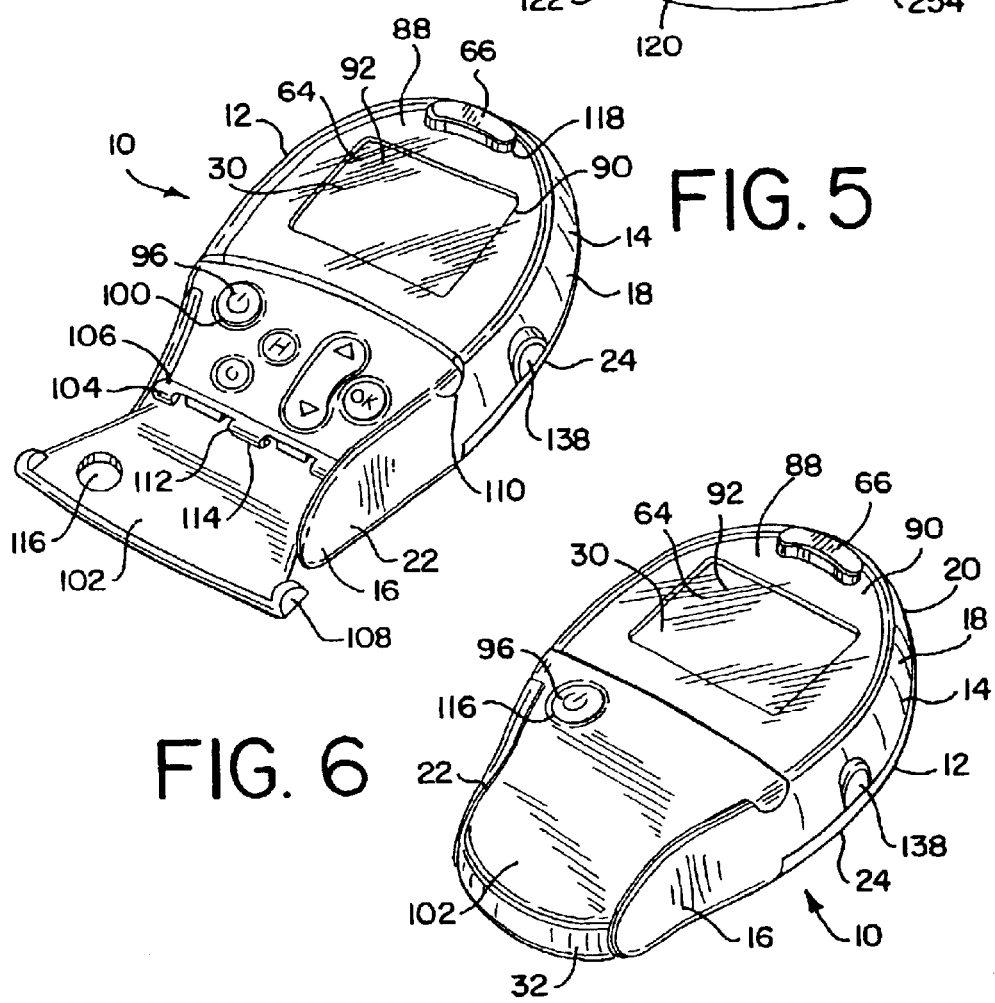

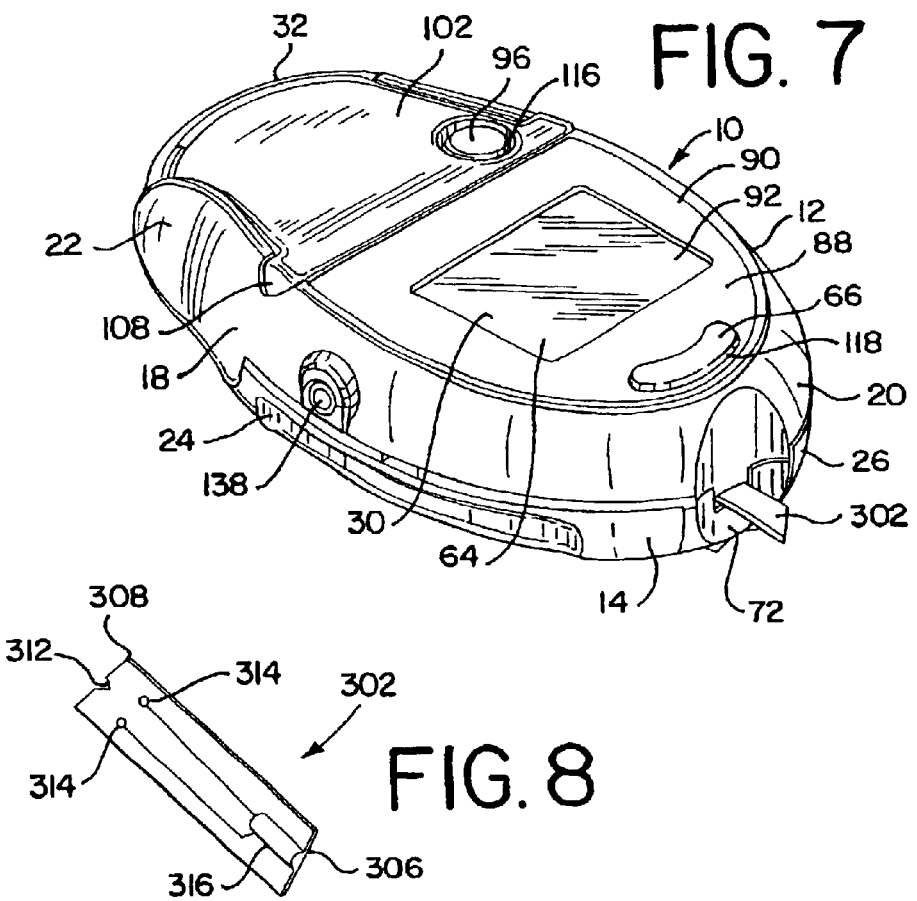
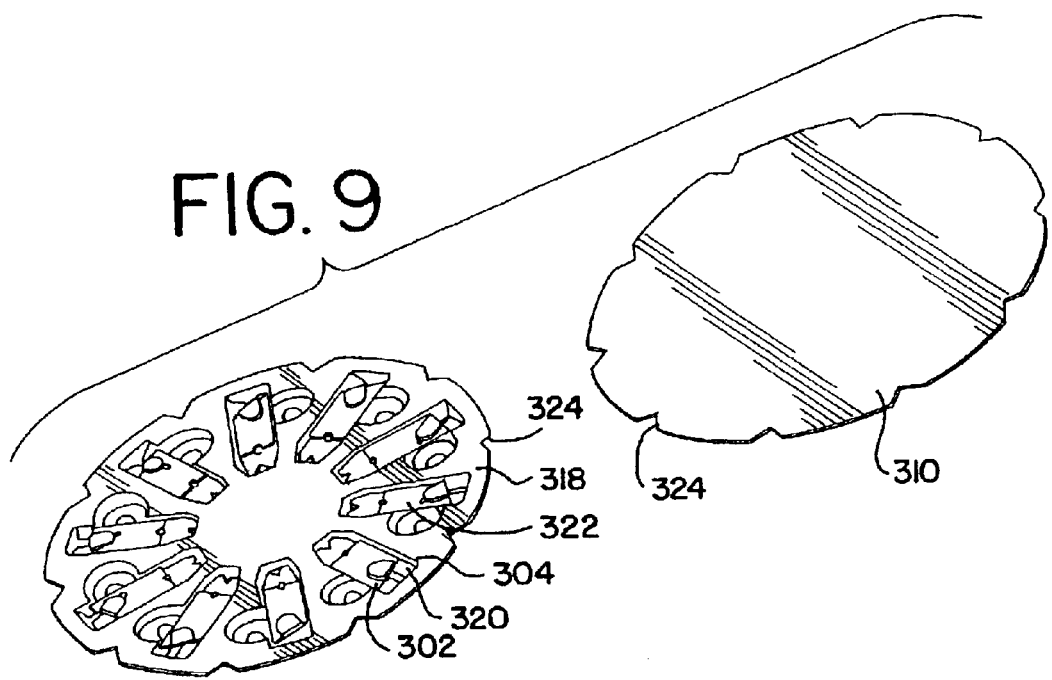

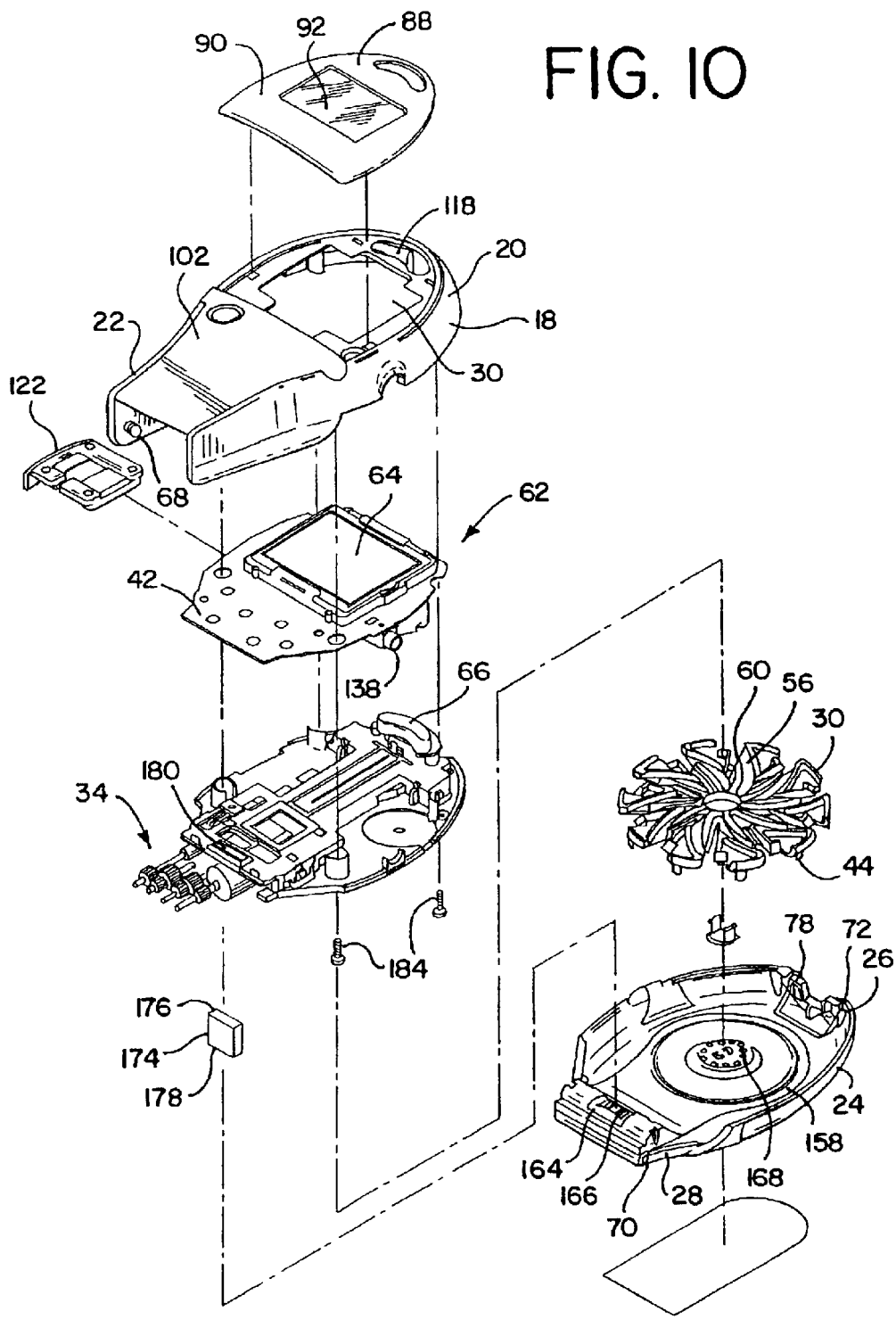

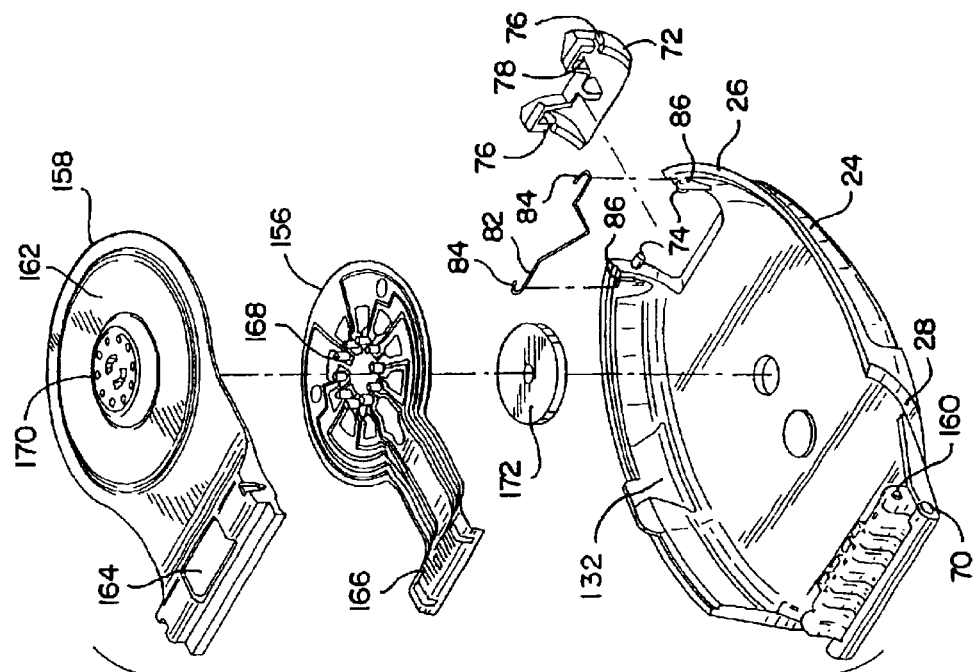

AUTOMATED MECHANICAL MECHANISM FOR A BLOOD GLUCOSE SENSOR DISPENSING INSTRUMENT

This application is a Provisional application No. 60/311,759, entitled "MECHANICAL MECHANISM FOR A BLOOD GLUCOSE SENSOR DISPENSING INSTRUMENT," filed on Aug. 13, 2001 which was converted to a regular application on Jul. 26, 2002 and given Ser. No. (not yet received), pending, which is incorporated by reference herein.

BACKGROUND OF THE INVENTION

1. Field of the Invention

The present invention generally relates to a fluid monitoring system, and, more particularly, to a new and improved instrument for handling multiple sensors that are used in analyzing blood glucose or other analytes contained therein.

2. Description of the Prior Art

People suffering from various forms of diabetes routinely need to test their blood to determine the level of blood glucose. The results of such tests can be used to determine what, if any, insulin or other medication needs to be administered. In one type of blood glucose testing system, sensors are used to test a sample of blood.

Such a sensor may have a generally flat, rectangular shape with a front or testing end and a rear or contact end. The sensor contains biosensing or reagent material that will react with blood glucose. The testing end of the sensor is adapted to be placed into the fluid being tested, for example, blood that has accumulated on a person's finger after the finger has been pricked. The fluid is drawn into a capillary channel that extends in the sensor from the testing end to the reagent material by capillary action so that a sufficient amount of fluid to be tested is drawn into the sensor. The fluid then chemically reacts with the reagent material in the sensor with the result that an electrical signal indicative of the blood glucose level in the blood being tested is supplied to contact areas located near the rear or contact end of the sensor.

In order to couple the electrical signals produced at the sensor contacts to monitoring equipment, the sensors need to be inserted into sensor holders prior to the sensor end being placed into the fluid being tested. The holders have corresponding mating contact areas that become coupled to the contacts on the sensor when the sensor is inserted into the holder. Consequently, the holders act as an interface between the sensor and monitoring equipment that accumulates and/or analyzes the test results.

Prior to being used, the sensors need to be maintained at an appropriate humidity level so as to insure the integrity of the reagent materials in the sensor. Sensors can be packaged individually in tear-away packages so that they can be maintained at the proper humidity level. For instance, blister type packaging methods could be used. In this connection, the packages can include desiccant material to maintain the proper humidity in the package. In order for a person to use an individual sensor for testing blood glucose, the package must be opened by tearing the seal. Alternatively, some packages require the user to exert force against one side of the package resulting in the sensor bursting or rupturing the foil on the other side. As can be appreciated, the opening of these packages can be difficult. Moreover, once the package is opened, the user needs to be sure that the sensor is not damaged or contaminated as it is being placed into the sensor holder and used to test the blood sample.

U.S. Pat. No. 5,630,986, issued on May 20, 1997, and entitled Dispensing Instrument For Fluid Monitoring Sensors (referred to hereinafter as "the '986 patent"), discloses a type of sensor pack with multiple sensors and a testing blood glucose and dispensing instrument for handling the sensors contained in such a sensor pack. In particular, the sensor dispensing instrument disclosed in the '986 patent is adapted to receive a sensor pack containing a plurality of blood glucose sensors. The sensor pack includes a circular base having a plurality of sensor retaining cavities, each of which hold an individual sensor. Each of the sensors has a generally flat, rectangular shape with a front testing end through which fluid is drawn so as to react with a reagent material in the sensor and an opposite rear, contact end.

The sensor instrument disclosed in the '986 patent includes an outer housing having an upper and a lower case that are pivotable with respect to each other so that the sensor pack can be positioned in the housing on an indexing disk disposed in the housing. With the sensor pack loaded in the housing, a slide latch on a slide actuator disposed on the upper case of the housing controls whether the movement of the slide actuator places the instrument in a display mode or in a testing mode. The instrument is placed into its display mode when the slide latch is moved laterally and the slide actuator is pushed away from its standby position. When in the display mode, a person using the instrument can view data displayed on a display unit in the upper case and/or input data into the instrument.

The instrument is in its testing mode when the slide latch is in its normal position and the slide actuator is pushed towards its testing position. As the slide actuator is moved towards its actuated position, the driver with the knife blade thereon moves toward the testing position of the feed mechanism and the disk drive arm travels in a straight, radially extending groove in the indexing disk such that the disk is not rotated as the feeding mechanism is moving towards its testing position. The knife blade is moved towards one of the sensor cavities in the sensor pack and pierces the foil covering the sensor cavity so as to engage the sensor disposed in the cavity. As the slide actuator and the driver are pushed toward the actuated position of the actuator, the knife blade ejects the sensor out from the sensor cavity and into a testing position near the testing end of the sensor housing.

Once the blood analyzing test is completed, the slide actuator is moved in the opposite direction towards its standby position so that the sensor can be removed from the dispensing instrument. The continued retraction of the driver causes the indexing disk drive arm to travel along a curvilinearly extending groove in the indexing disk, resulting in the rotation of the indexing disk. The rotation of the indexing disk results in the sensor pack being rotated so that the next sensor is positioned in alignment with the knife blade for the next blood glucose test that is to be performed.

Although the sensor instrument disclosed in the '986 patent overcomes many of the problems discussed above in connection with the use of individual sensors, the sensor instrument disclosed in the '986 requires manual force to eject a sensor from the sensor cavity and into a testing position. The user must overcome this force with a thumb slide or a push-pull handle. Some users of have experienced difficulties in the operation and/or manipulation of the disclosed sensor instruments. For example, users with limited dexterity may find the manipulation of the slide latch or the push-pull handle difficult. Similarly, some users, elderly users in particular, may find the operation of these devices complicated or confusing. This may lead to user errors in the manipulation of the slide latch or the push-pull mechanism, which can result in a jam in the operation of the device.

Accordingly, it is desirable to have a sensor dispensing instrument utilizing an improved mechanical mechanism that can be more easily manipulated by users with limited dexterity, and is less likely to jam as the result of user error.

In addition, some users have encountered spoiled sensors resulting from partial or incorrect manipulation of the device. This is because a new sensor is moved into alignment with the knife blade at the conclusion of each test. If, for example, a user intending to activate the display mode of the device accidentally moves the slide latch into the testing mode direction, the knife blade may puncture the foil covering the sensor cavity of the new sensor. Even if the user realizes the error and returns the slide latch to the neutral position, the sensor in the punctured sensor cavity will be exposed to the humidity in the air and must be used immediately or discarded. Accordingly, it is desirable to have a sensor dispensing instrument utilizing an improved mechanical mechanism that will eliminate inadvertent spoilage of sensors as the result of user error.

BRIEF SUMMARY OF THE INVENTION

Accordingly, an object of the present invention is to provide a new and improved sensor dispensing instrument for handling the sensors contained in a sensor pack of multiple sensors used in testing blood glucose. In particular, objects of the present invention are to provide a new and improved fluid sensor dispensing instrument handling device having a mechanical mechanism that can be more easily operated by a user with limited finger strength or dexterity, that reduces the possibility of jams, eliminates the spoilage of sensors because of user error, and which otherwise overcomes the problems or limitations discussed above.

In accordance with these and many other objects of the present invention, the present invention is embodied in a sensor dispensing instrument that is adapted to handle a sensor pack containing a plurality of sensors, each of the plurality of sensors being disposed in a sensor cavity on the sensor pack and enclosed by a protective foil covering. The sensor dispensing instrument is further adapted to perform a test using one of the sensors. The sensor dispensing instrument includes an outer housing having a front end and a rear end, and a sensor opening through which one of said sensors is disposed to conduct the test. The sensor opening is disposed at the front end of the outer housing. The sensor dispensing instrument also includes a motor, a power transfer system and a linear drive system within the outer housing. The power transfer system is connected with the motor and the linear drive system for transferring power from the motor to the linear drive system. The sensor dispensing instrument also includes a disk drive mechanism generally disposed within the outer housing and connected to the linear drive system. The disk drive mechanism includes a disk drive pusher, wherein the linear drive system moves the disk drive pusher when the motor is activated.

In accordance with another aspect of the present invention, the present invention is embodied in a method of operating a sensor dispensing instrument that is adapted to handle a sensor pack containing a plurality of sensors and to perform a test using one of the sensors, wherein the sensor dispensing instrument includes an outer housing having a sensor opening through which one of the sensors is disposed to conduct the test, a disk drive mechanism having an indexing disk for supporting and rotating the sensor pack, an indexing disk drive arm for rotating the indexing disk, a knife blade assembly for puncturing the foil covering and ejecting one of the sensors from the sensor cavity and through the sensor opening, and a disk drive pusher for moving the indexing disk drive arm and the knife blade assembly. The method comprises the steps of: a) pressing said button to cause a motor within said sensor dispensing instrument activate, wherein the motor causes said indexing disk drive arm to move and rotate said indexing disk and align the sensor cavity with the sensor opening, and causes the knife blade assembly to puncture the foil covering and eject the sensor from the sensor cavity and through said sensor opening; b) performing the test by using the sensor disposed in said sensor opening; and c) pressing another button that causes the knife blade assembly to move forward even more, pushing and subsequently ejecting the sensor from the sensor opening.

BRIEF DESCRIPTION OF SEVERAL VIEWS OF THE DRAWINGS

The present invention, together with the above and other objects and advantages, can best be understood from the following detailed description of the embodiment of the invention illustrated in the drawing, wherein:

FIG. 1 is a top perspective view of a blood glucose sensor dispensing instrument embodying the present invention;

FIG. 2 is a bottom perspective view of the blood glucose sensor dispensing instrument of FIG. 1;

FIG. 3 is a perspective view of the blood glucose sensor dispensing instrument of FIG. 1 in the opened position showing the insertion of a sensor pack;

FIG. 4 is a perspective view of the blood glucose sensor dispensing instrument of FIG. 1 in the opened position showing a sensor pack loaded onto the indexing disk;

FIG. 5 is a top perspective view of the blood glucose sensor dispensing instrument of FIG. 1 shown with the button door in the open position;

FIG. 6 is a top perspective view of the blood glucose sensor dispensing instrument of FIG. 1 with the disk drive pusher in the extended position;

FIG. 7 is a top perspective view of the blood glucose sensor dispensing instrument of FIG. 1 with the disk drive pusher in the testing position with a sensor projecting from the sensor opening;

FIG. 8 is a top perspective view of a sensor for use with blood glucose sensor dispensing instrument of FIG. 1;

FIG. 9 is an exploded perspective view of a sensor pack for use with blood glucose sensor dispensing instrument of FIG. 1 showing the protective foil separated from the base portion of the sensor pack;

FIG. 10 is an exploded perspective view of the component subassemblies of blood glucose sensor dispensing instrument of FIG. 1;

FIG. 11 is an exploded perspective view of the component parts of the upper case sub-assembly of the blood glucose sensor dispensing instrument of FIG. 1;

FIG. 12 is an exploded perspective view of the component parts of the lower case sub-assembly of the blood glucose sensor dispensing instrument of FIG. 1;

DETAILED DESCRIPTION OF THE INVENTION

Figure 13:
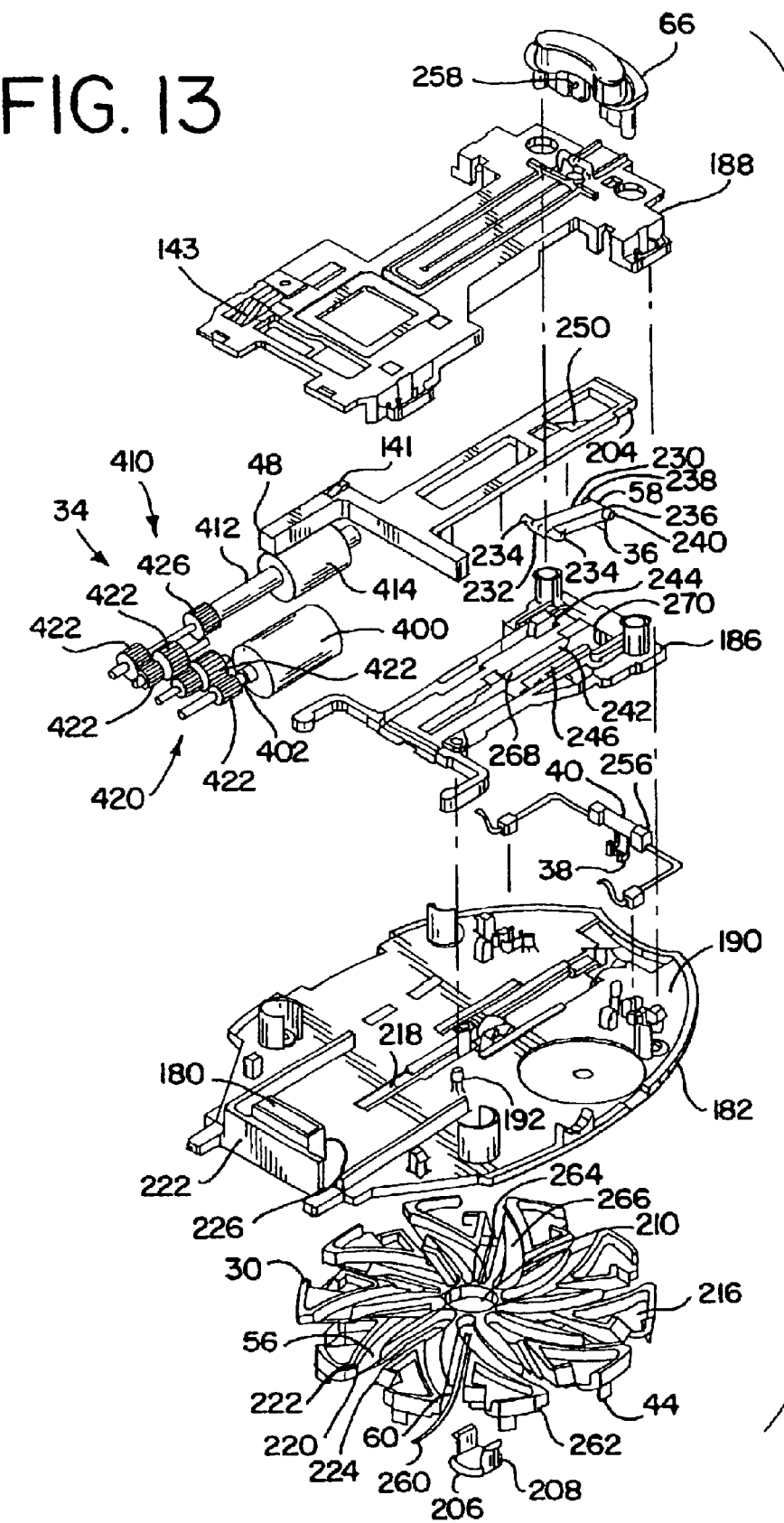
FIG. 13 is an exploded top perspective view of the component parts of the disk drive mechanism and indexing disk sub-assembly of the blood glucose sensor dispensing instrument of FIG. 1.

Referring now more specifically to the drawings, therein is disclosed a blood glucose sensor dispensing instrument generally designated by the reference numeral 10 and embodying the present invention. The sensor dispensing instrument 10 includes an outer housing 12 having an upper case 18 and a lower case 24, the lower case 24 pivoting on the upper case 18. The upper case 18 is pivotable with respect to the lower case 24 in a clamshell fashion so that a sensor pack 300 (see FIGS. 3 and 4) can be positioned on an indexing disk 30 within the housing 12. With the sensor pack 300 so loaded in the housing 12, a button 32 can be pressed to cause a disk drive mechanism, generally designated by the numeral 34 (see FIG. 10), to load a sensor 302 into a testing position on the front end 14 of the housing 12 (see FIG. 3). The sensor dispensing instrument also includes a motor 400, a linear drive system 410, and a power transfer system 420, which cause the disk drive mechanism 34 to load a sensor 302 into a testing position on the front end 14 of the, housing once the button 32 is pressed, as described below.

It should be noted that the sensor dispensing instrument 10 of the present invention incorporates components that are similar in design and/or function as those described in U.S. Pat. No. 5,630,986, issued May 20, 1997, and entitled Dispensing Instrument For Fluid Monitoring Sensors. The contents of these patents are hereby incorporated by reference to avoid the unnecessary duplication of the description of these similar components.

The sensor pack 300 utilized by the sensor dispensing instrument 10 is of the type described in U.S. Pat. No. 5,575,403, issued Nov. 19, 1996, and entitled Dispensing Instrument For Fluid Monitoring Sensors, the contents of which are hereby incorporated by reference. In general, and as shown in FIGS. 8 and 9, the sensor pack 300 is adapted to house ten sensors 302, with one of the ten sensors 302 in each of ten separate sensor cavities 304. Each of the sensors 302 has a generally flat, rectangular shape extending from a front or testing end 306 to a back end 308. The front end 306 is angled so that it will puncture an unsevered portion of the protective foil 310 overlying the sensor cavity 304 as the sensor 302 is being forced out of the sensor cavity 304 by a knife blade 36 (to be described below). The front end 306 is also adapted to be placed into blood that is being analyzed. The back end 308 of the sensor 302 includes a small notch 312 that is engaged by the knife blade 36 as the knife blade 36 ejects the sensor 302 from the sensor cavity 304. Contacts 314 near the back end 308 of the sensor 302 are adapted to mate with metal contacts 38 on a sensor actuator 40 (to be described below) when the sensor 302 is in the testing position illustrated in FIG. 7. As a result, the sensor 302 is coupled to the electronic circuitry on the circuit board assembly 42 so that information generated in the sensor 302 during testing can be stored, analyzed and/or displayed.

As best seen in FIG. 8, each sensor 302 is provided with a capillary channel 316 that extends from the front or testing end 306 of the sensor 302 to biosensing or reagent material disposed in the sensor 302. When the testing end 306 of the sensor 302 is placed into fluid (for example, blood that is accumulated on a person's finger after the finger has been pricked), a portion of the fluid is drawn into the capillary channel 316 by capillary action. The fluid then chemically reacts with the reagent material in the sensor 302 so that an electrical signal indicative of the blood glucose level in the blood being tested is supplied to the contacts 314, and subsequently transmitted through the sensor actuator 40 to the circuit board assembly 42.

As best seen in FIG. 9, the sensor pack 300 comprises a circularly shaped base portion 318 covered by a sheet of protective foil 310. The sensor cavities 304 are formed as depressions in the base portion 318, with each of the sensor cavities 304 adapted to house an individual sensor 302. Each of the sensor cavities 304 has an inclined or sloped support wall 320 to guide the sensor 302 as the sensor 302 is ejected through the foil 310 and out of the sensor cavity 304.

Each of the sensor cavities 304 is in fluid communication with a desiccant cavity 322 formed by a small depression in the base portion 318. Desiccant material is disposed in each of the desiccant cavities 322 in order to insure that the sensor cavities 304 are maintained at an appropriate humidity level to preserve the reagent material in the sensor 302.

Notches 324 are formed along the outer peripheral edge of the base portion 318. The notches 324 are configured to engage pins 44 on the indexing disk 30 so that the sensor cavities 304 are in proper alignment with the indexing disk 30 when the sensor pack 300 is loaded into the sensor dispensing instrument 10. As will be explained in greater detail below, the sensor cavities 304 must be aligned with the knife slots 46 in the indexing disk 30 to permit the knife blade 36 to engage, eject and push one of the sensors 302 into a testing position on the front end 14 of the housing 12.

The sensor pack 300 further comprises a conductive label 326 on the central portion of the base portion 318. As will be explained below, the conductive label 326 provides calibration and production information about the sensor pack 300 that can be sensed by calibration circuitry in the sensor dispensing instrument 10.

To operate the sensor dispensing instrument 10, the button 32 is pressed causing an electrical connection (not shown) between the button 32 and a motor 400 (FIG. 14B) to be made, and therefore causing the motor 400 to be activated. Upon activation, the motor 400 moves a linear drive system 410 (FIG. 14B) which causes the disk drive mechanism 34 to rotate the sensor pack 300 and place the next sensor 302 in a standby position prior to being loaded into a testing position. The pressing of the button 32 also causes the sensor dispensing instrument 10 to turn ON (i.e., the electronic circuitry on the circuit board assembly 42 is activated).

As will be described in greater detail below, the disk drive mechanism 34 includes a disk drive pusher 48 on which an indexing disk drive arm 50 is mounted (see FIGS. 13 and 14A). The indexing disk drive arm 50 comprises a cam button 52 disposed at the end of a plate spring 54. The cam button 52 is configured to travel in one of a plurality of curvilinearly extending grooves 56 on the upper surface of the indexing disk 30. As the button 32 is pressed, the motor 400 is activated, causing the linear drive system 410 to move the disk drive pusher 48 laterally towards the rear end 22 of the upper case 18. This causes the cam button 52 on the indexing disk drive arm 50 to travel along one of the curvilinearly extending grooves 56 so as to rotate the indexing disk 30. The rotation of the indexing disk 30 causes the sensor pack 300 to be rotated so that the next one of the sensor cavities 304 is placed in a standby position.

The linear drive system 410 then moves the disk drive pusher 48 laterally towards the front end 14 of the upper case 18 and causes the disk drive mechanism 34 to remove a sensor 302 from the sensor pack 300 and place the sensor 302 into a testing position on the front end 14 of the housing 12.

The linear drive system 410 then moves the disk drive pusher 48 towards the front end 14 of the upper case 18 even more causing the sensor 302 to be pushed forward out of the sensor opening 254 so that the sensor 302 is free from the instrument 10 and can be disposed.

As will be described in greater detail below, the disk drive mechanism 34 includes a knife blade assembly 58 that is pivotally mounted to the disk drive pusher 48 (see FIGS. 13 and 14A). After the disk drive pusher 48 is moved laterally towards the rear end 22 of the upper case 18, the disk drive pusher 48 is then pushed laterally towards the testing or front end 20 of the upper case 18. This causes the knife blade assembly 58 to pivot downwardly so that a knife blade 36 on the end of the knife blade assembly 58 pierces a portion of the protective foil 310 covering one of the sensor cavities 304 and engages the sensor 302 in the sensor cavity 304. As the disk drive pusher 48 continues to move towards the front end 20 of the upper case 18, the knife blade assembly 58 forces the sensor 302 out of the sensor cavity 304 and into a testing position at the front end 14 of the housing 12.

While the disk drive pusher 48 is being moved from the extended position to the testing position, the cam button 52 on the indexing disk drive arm 50 travels along one of the radially extending grooves 60 to prevent the indexing disk 30 from rotating. Similarly, while the disk drive pusher 48 is being moved from the standby position to the extended position, the knife blade assembly 58 is in a retracted position so as to not interfere with the rotation of the indexing disk 30.

After the sensor 302 has been completely ejected from the sensor cavity 304 and pushed into a testing position projecting out from the front end 14 of the housing 12, the disk drive pusher 48 engages and forces a sensor actuator 40 against the sensor 302 to thereby maintain the sensor 302 in the testing position. The sensor actuator 40 engages the sensor 302 when the button 32 is pressed. The sensor actuator 40 couples the sensor 302 to an electronics assembly 62 disposed in the upper case 18. The electronics assembly 62 includes a microprocessor or the like for processing and/or storing data generated during the blood glucose test procedure, and displaying the data on a liquid crystal display 64 in the sensor dispensing instrument 10.

Once the blood analyzing test is completed, a button release 66 on the upper case 18 is depressed so as to disengage the sensor actuator 40 and release the sensor 302. Depressing the button release 66 causes the disk drive pusher 48 and the button 32 to move forward pushing the sensor 302 out of the sensor opening 254 and then move back to the standby position. At this point, the user can turn the sensor dispensing instrument 10 OFF by depressing the button 96 on the upper case 18, or by allowing the sensor dispensing instrument 10 automatically turn OFF pursuant a timer on the electronics assembly 62.

As seen in FIGS. 1–7 and 10–12, the upper case 18 and the lower case 24 of the sensor dispensing housing 12 are complementary, generally oval shaped hollow containers that are adapted to be pivoted with respect to each other about pivot pins 68 extending outwardly in the rear end 22 of the upper case 18 into pivot holes 70 in a rear section 28 of the lower case 24. The upper case 18 and the lower case 24 are maintained in their closed configuration by a latch 72 that is pivotally mounted in a front section 26 of the lower case 24 by pins 74 that extend inwardly into pivot holes 76 in the latch 72 (see FIG. 12). The latch 72 has recesses 78 that are configured to mate with hooks 80 on the upper case 18 to secure the upper case 18 and the lower case 24 in their closed configuration. The latch 72 is biased in a vertical or closed position by a latch spring 82. The ends 84 of the latch spring 82 are secured in slots 86 on the inside of the lower case 24. When the latch 72 is pivoted against the biasing force of the latch spring 82, the hooks 80 on the upper case 18 disengage from the recesses 78 to permit the upper case 18 and the lower case 24 to open.

As seen in FIGS. 1, 5–7 and 10–11, the upper case 18 includes a rectangular opening 30 through which a liquid crystal display 64 is visible below. The liquid crystal display 64 is visible through a display lens 88 that is affixed to upper surface of the upper case 18. In the preferred embodiment shown, the display lens 88 has an opaque portion 90 and a transparent portion 92, the transparent portion 92 being coincident with the display area of liquid crystal display 64. The liquid crystal display 64 is a component of the electronics assembly 62, and is coupled to the circuit board assembly 42 via elastomeric connectors 94 (see FIG. 16). The liquid crystal display 64 displays information from the testing procedure and/or in response to signals input by the buttons 96 on the upper case 18. For example, the buttons 96 can be depressed to recall and view the results of prior testing procedures on the liquid crystal display 64. As best seen in FIG. 11, the buttons 96 are part of a button set 98 that is attached to the upper case 18 from below so that the individual buttons 96 project upwardly through button openings 100 in the upper case 18. When pressed, the buttons 96 are electrically connected to the circuit board assembly 42.

As best seen in FIGS. 1, 5 and 11, a button door 102 is pivotally connected to the upper case 18 by a pair of pins 104 projecting outwardly from either side of the button door 102 that engage holes 106 on the side walls of the upper case 18. The button door 102 also comprises a pair of ears 108 that fit into recesses 110 in the side walls of the upper case 18 when the button door 102 is closed. The ears 108 extend slightly beyond the side walls of the upper case 18 so that they can be grasped by the user to open the button door 102. A pivot edge 112 of the button door 102 engages a tab 114 on the upper surface of the upper case 18. The tab 114 rubs against the pivot edge 112 in such a manner so as to bias the button door 102 in either a closed or fully open position. In the preferred embodiment shown, the button door 102 has an opening 116 that permits one of the buttons 96 (e.g., an On/Off button) to be accessed when the button door 102 is closed (see FIG. 1). This permits dedicated, but seldom or lesser used buttons 96 to be concealed underneath the button door 102, thereby simplifying the learning curve and daily operation of the sensor dispensing instrument 10 for the user.

The upper case 18 also contains an opening 118 for the button release 66, which projects upwardly through the upper case 18. As will be described in more detail below, the button release 66 is depressed to disengage the sensor actuator 40 and release a sensor 302 from the testing position.

The upper case 18 also contains an opening 120 for a battery tray assembly 122. The battery tray assembly 122 includes a battery tray 124 in which a battery 126 is disposed. The batter tray assembly 122 is inserted into the opening 120 in the side of the upper case 18. When so inserted, the battery 126 engages battery contacts 128 and 130 on the circuit board assembly 42 so as to provide power for the electronics within the instrument 10, including the circuitry on the circuit board assembly 42 and the liquid crystal display 64, and the power for the motor 400. A tab 132 on the lower case 24 is configured to engage a slot 134 in the battery tray assembly 122 so as to prevent the battery tray assembly 122 from being removed from the sensor dispensing instrument 10 when the upper case 18 and the lower case 24 are in the closed configuration.

Figure 16:
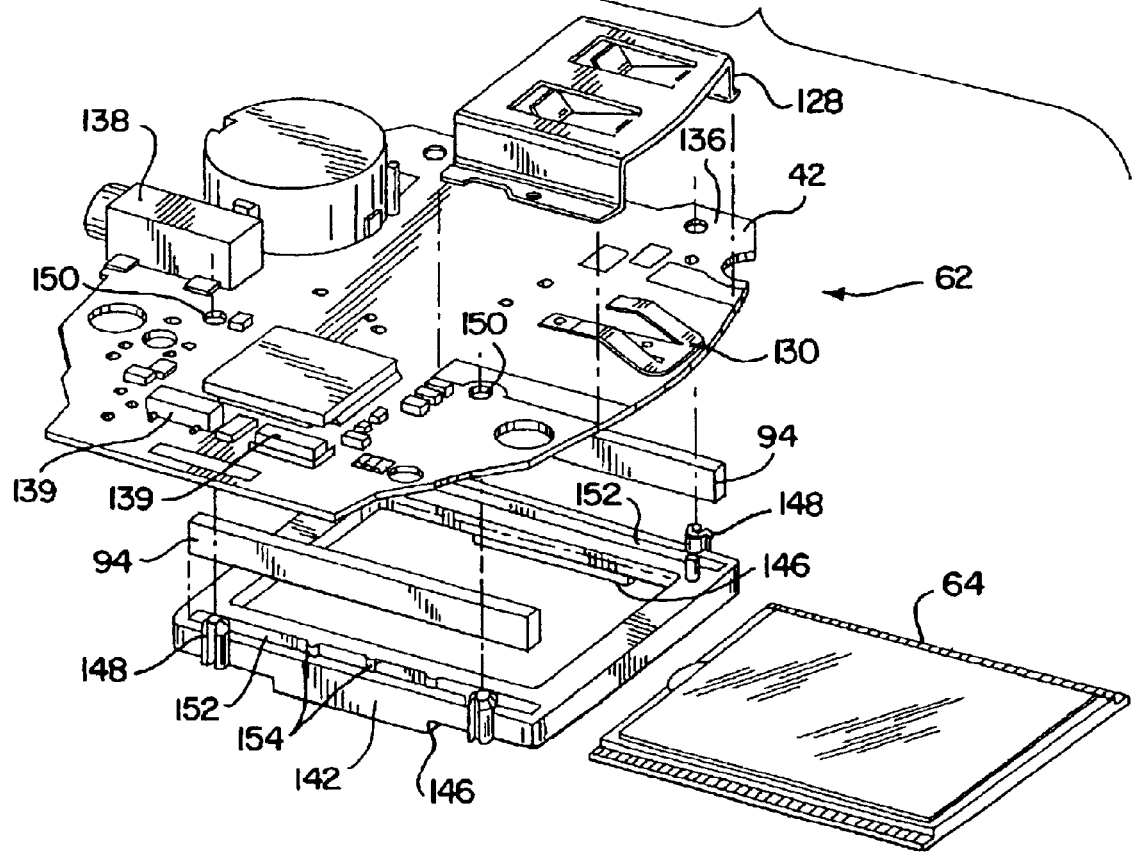
FIG. 16 is an exploded perspective view of the component parts of the electronics assembly of the blood glucose sensor dispensing instrument of FIG. 1.
Figure 17:
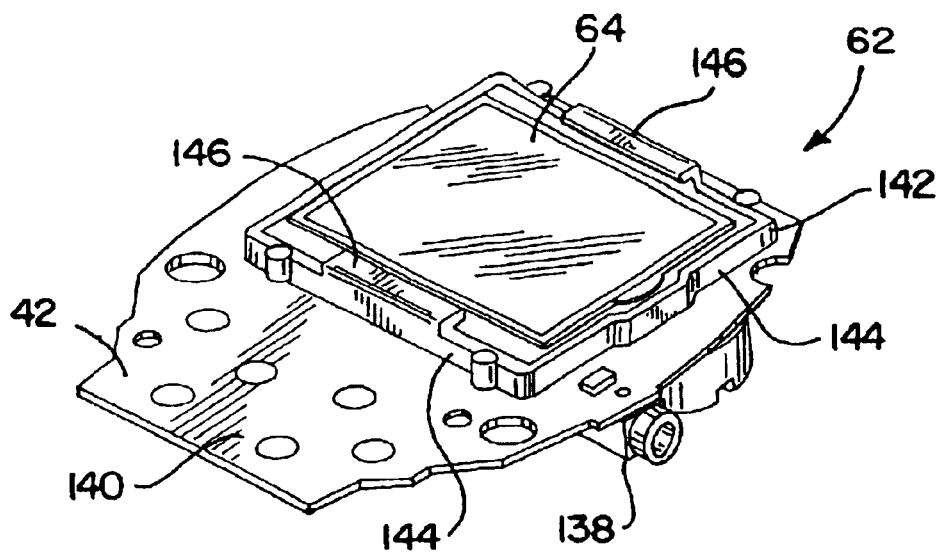
FIG. 17 is a top perspective view of the electronics sub-assembly of the blood glucose sensor dispensing instrument of FIG. 1.
Figure 18:
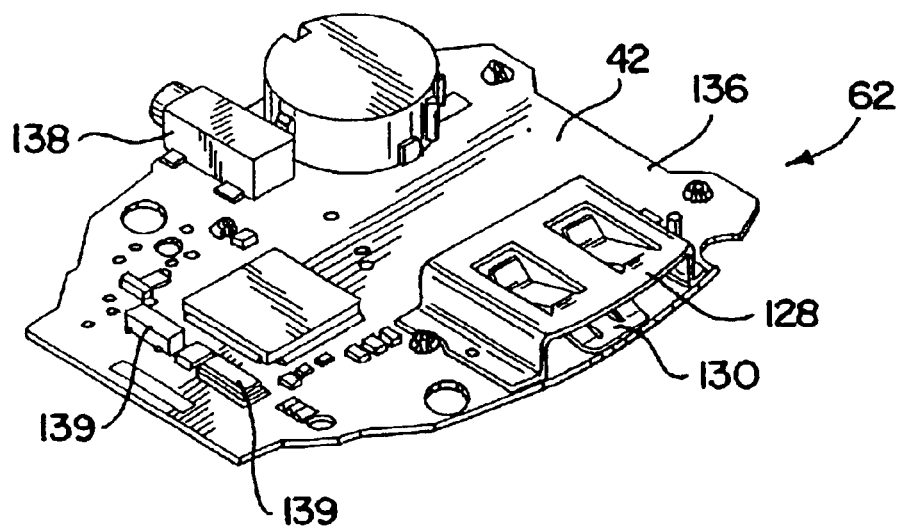
FIG. 18 is a bottom perspective view of the electronics sub-assembly of the blood glucose sensor dispensing instrument of FIG. 1.

An electronics assembly 62 is affixed to the upper inside surface of the upper case 18. As best seen in FIGS. 16–18, the electronics assembly 62 comprises a circuit board assembly 42 on which various electronics and electrical components are attached. A positive battery contact 128 and a negative battery contact 130 are disposed on the bottom surface 136 (which is the upwardly facing surface as viewed in FIGS. 16 and 18) of the circuit board assembly 42. The battery contacts 128 and 130 are configured to electrically connect with the battery 126 when the battery tray assembly 122 is inserted into the side of the upper case 18. The bottom surface 136 of the circuit board assembly 42 also includes a communication interface 138. The communication interface 138 permits the transfer of testing or calibration information between the sensor dispensing instrument 10 and another device, such as a personal computer, through standard cable connectors (not shown). In the preferred embodiment shown, the communication interface 138 is a standard serial connector. However, the communication interface 138 could alternatively be an infra-red emitter/detector port, a telephone jack, or radio frequency transmitter/receiver port. Other electronics and electrical devices, such as memory chips for storing glucose test results or ROM chips for carrying out programs, are likewise included on the bottom surface 136 and the upper surface 140 of the circuit board assembly 42.

A liquid crystal display 64 is affixed to the upper surface 140 (upwardly facing surface in FIG. 17) of the circuit board assembly 42. The liquid crystal display 64 is held by a snap-in display frame 142. The snap-in display frame 142 includes side walls 144 that surround and position the liquid crystal display 64. An overhang 146 on two of the side walls 144 holds the liquid crystal display 64 in the snap-in display frame 142. The snap-in display frame 142 includes a plurality of snap fasteners 148 that are configured to engage mating holes 150 on the circuit board assembly 42. The liquid crystal display 64 is electrically connected to the electronics on the circuit board assembly 42 by a pair of elastomeric connectors 94 disposed in slots 152 in the snap-in display holder 142. The elastomeric connectors 94 generally comprise alternating layers of flexible conductive and insulating materials so as to create a somewhat flexible electrical connector. In the preferred embodiment shown, the slots 152 contain a plurality of slot bumps 154 that engage the sides of the elastomeric connectors 94 to prevent them from falling out of the slots 152 during assembly.

The snap-in display frame 142 eliminates the screw-type fasteners and metal compression frames that are typically used to assemble and attach a liquid crystal display 64 to an electronic device. In addition, the snap-in display frame 142 also permits the liquid crystal display 64 to be tested prior to assembling the liquid crystal display 64 to the circuit board assembly 42.

The button set 98 also mates to the upper surface 140 of the circuit board assembly 42. As mentioned above, the button set 98 comprises several individual buttons 96 that are depressed to operate the electronics of the sensor dispensing instrument 10. For example, the buttons 96 can be depressed to activate the testing procedure of the sensor dispensing instrument 10. The buttons 96 can also be depressed to recall and have displayed on the liquid crystal display 64 the results of prior testing procedures. The buttons 96 can also be used to set and display date and time information, and to activate reminder alarms which remind the user to conduct a blood glucose test according to a predetermined schedule. The buttons 96 can also be used to activate certain calibration procedures for the sensor dispensing instrument 10.

The electronics assembly 62 further comprises a pair of surface contacts 139 on the bottom surface 136 of the circuit board assembly 42 (see FIGS. 16 and 18). The surface contacts 139 are configured so as to be contacted by one or more fingers 143 on the cover mechanism 188, which in turn are configured to be engaged by a pair of ramp contacts 141 on the disk drive pusher 48 (see FIGS. 6 and 13). Movement of the disk drive pusher 48 causes the ramp contacts 141 to push the fingers 143 into contact with one or both of the surface contacts 139 so as to communicate the position of the pusher 48 to the electronics assembly 62. In particular, movement of the pusher 48 from a stand-by or testing positions to an extended position will turn the sensor dispensing instrument ON. In addition, if the housing 12 is opened while the pusher 48 is in the extended position, an alarm will be activated to warn the user that the knife blade 36 may be in the extended position.

It should be noted that the design and configuration of the electronics assembly 62 permits the assembly and testing of the electronics and electrical components prior to assembly of the electronics assembly 62 to the upper case 18 of the sensor dispensing instrument 10. In particular, the liquid crystal display 64, the button set 98, the battery contacts 128 and 130, and the other electronics and electrical components can each be assembled to the circuit board assembly 42 and tested to verify that these components, and the electrical connections to these components, are working properly. Any problem or malfunction identified by the testing can then be corrected, or the malfunctioning component can be discarded, prior to assembling the electronics assembly 62 to the upper case 18 of the sensor dispensing instrument 10.

As mentioned above, the sensor dispensing instrument 10 includes calibration circuitry for determining calibration and production information about the sensor pack 300. As best seen in FIG. 12, the calibration circuitry comprises a flex circuit 156 located in the lower case 24. The flex circuit 156 is held in position in the lower case 24 by an autocal disk 158 that is connected to the rear section 28 of the lower case 24 by a pair of pins 160. The autocal disk 158 has a raised central portion 162 configured to engage the sensor cavities 304 on the sensor pack 300 so as to hold the sensor pack 300 against the indexing disk 30. The autocal disk 158 also has an open area 164 located between the pins 160 to expose contacts 166 on the flex circuit 156.

The flex circuit 156 comprises a plurality of probes 168 that extend upwardly from the flex circuit 156 through holes 170 in the inner region of the autocal disk 158. These probes 168 are connected to the contacts 166 of the end of the flex circuit 156. When the sensor dispensing instrument 10 is closed with the lower case 24 latched to the upper case 18, the probes 168 make contact with a conductive label 326 on the sensor pack 300 being used in the sensor dispensing instrument 10. A foam pad 172 is positioned below the flex circuit 156 to provide a biasing force to assure that the probes 168 press against the conductive label 326 with a force sufficient to make an electrical connection. The foam pad 172 also provides a cushioning force so that the probes 168 can move independently with respect to each other as the sensor pack 300 is being rotated by the indexing disk 30. As a result, information, such as calibration and production data, contained on the conductive label 326 can be transmitted via the probes 168 to the flex circuit 156, which in turn couples the data to the electronic circuitry on the circuit board assembly 42 via an elastomeric connector 174. This information can then be used by the electronics assembly 62 to calibrate the sensor dispensing instrument 10, or can be displayed on the liquid crystal display 64.

As best seen in FIG. 10, the elastomeric connector 174 is made of layers of silicon rubber extending from a top edge 176 to a bottom edge 178 with alternate layers having conductive materials dispersed therein to connect contacts on the top edge 176 to contacts on the bottom edge 178. When the upper case 18 and the lower case 24 are closed, the elastomeric connector 174 is compressed in the direction between the edges 176 and 178 such that the contacts along the top edge 176 engage electronic circuitry on the circuit board assembly 42 in the upper case 18, and the contacts along the bottom edge 178 engage the contacts 166 on the flex circuit 156 in the lower case 24. With the elastomeric connector 174 so compressed, low voltage signals can be readily transmitted between the circuit board assembly 42 and the flex circuit 156 through the elastomeric connector 174.

The elastomeric connector 174 is held in position by a slotted housing 180 on the guide block 182. In the preferred embodiment shown, the slotted housing 180 has a serpentine cross-section configured to allow the connector 174 to compress when the upper case 18 and the lower case 24 are closed, while still holding the elastomeric connector 174 when the upper case 18 and the lower case 24 are open. Alternatively, the slotted housing 180 may include inwardly projecting ridges that engage the sides of the connector 174.

The disk drive mechanism 34 is affixed to the upper inside surface of the upper case 18. As best seen in FIG. 10, the disk drive mechanism 34 is attached to the upper case by a plurality of mounting screws 184 that engage posts (not shown) on the upper inside surface of the upper case 18. The mounting screws 184 also pass through and secure the electronics assembly 62, which is disposed between the disk drive mechanism 34 and the upper case 18.

Although the disk drive mechanism 34 will be described in greater detail below, it should be noted that preferably the disk drive mechanism 34 is configured so as to permit the assembly and testing of its operation prior to mounting the disk drive mechanism 34 to the upper inside surface of the upper case 18. In other words, preferably the disk drive mechanism 34 has a modular design that can be tested prior to final assembly of the sensor dispensing instrument 10.

Figure 14A:
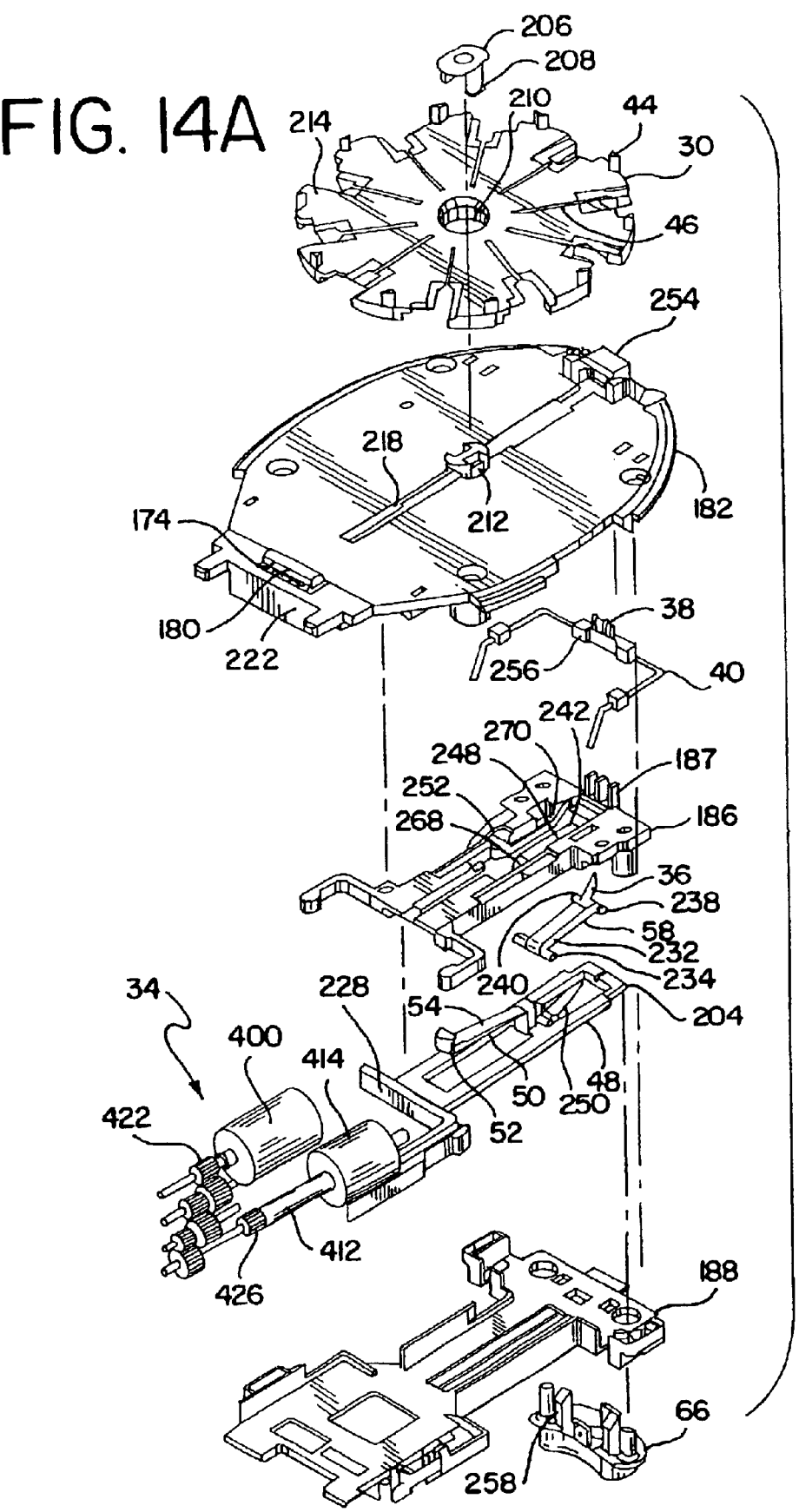
FIG. 14A is an exploded bottom perspective view of the component parts of the disk drive mechanism and indexing disk sub-assembly of the blood glucose sensor dispensing instrument of FIG. 1.

As best seen in FIGS. 13 and 14A, the disk drive mechanism 34 comprises a guide block 182, a sensor actuator 40, a housing guide 186, a disk drive pusher 48, an indexing disk drive arm 50, a knife blade assembly 58, a cover mechanism 188, and a button release 66. The housing guide 186 is fixed to the upper surface 190 (as viewed in FIG. 13) of the guide block 182 by one or more pins 192. The disk drive pusher 48 is supported on the housing guide 186 and the guide block 182 in such a manner as to permit the disk drive pusher 48 to slide laterally relative to the housing guide 186 and the guide block 182. The knife blade assembly 58 is pivotally connected to the underside of the disk drive pusher 48, and is guided by the housing guide 186 and the guide block 182. The indexing disk drive arm 50 is also connected to the disk drive pusher 48, and is partially guided by the guide block 182. The cover mechanism 188 is affixed to the guide block 182 with the disk drive pusher 48 and the housing guide 186 disposed therebetween. The sensor actuator 40 is attached to the guide block 182 and is engaged by the front end 204 of the disk drive pusher 48 when the disk drive pusher 48 is in the testing position. The button release 66 is slidably connected to the cover mechanism 188 so as to engage the front end 204 of the disk drive pusher 48 when the disk drive pusher 48 is in the testing position.

Figure 14B:
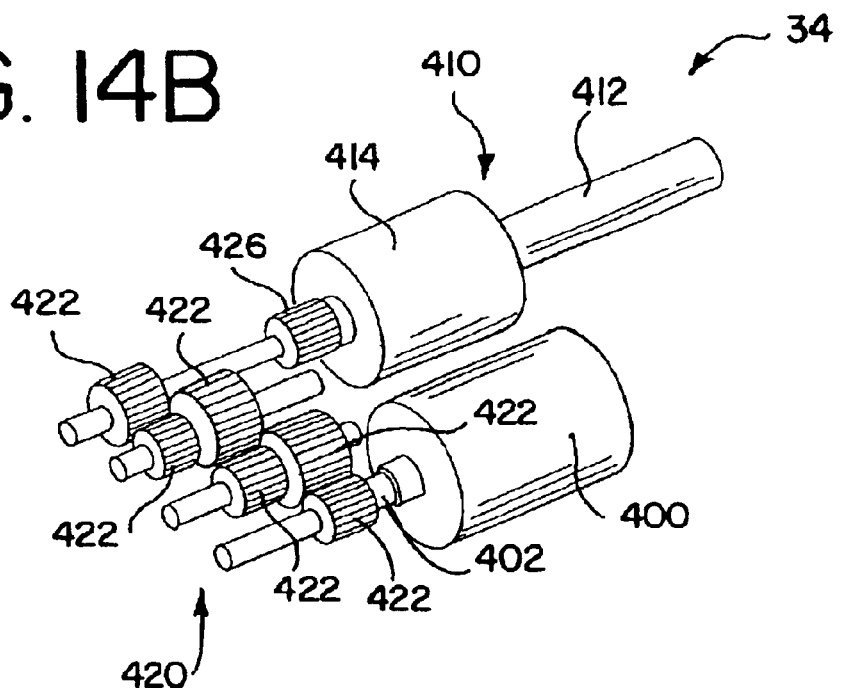
FIG. 14B is a perspective view of the component parts of the disk drive mechanism of the blood glucose sensor dispensing instrument of FIG. 1, according to one embodiment.
Figure 14C:
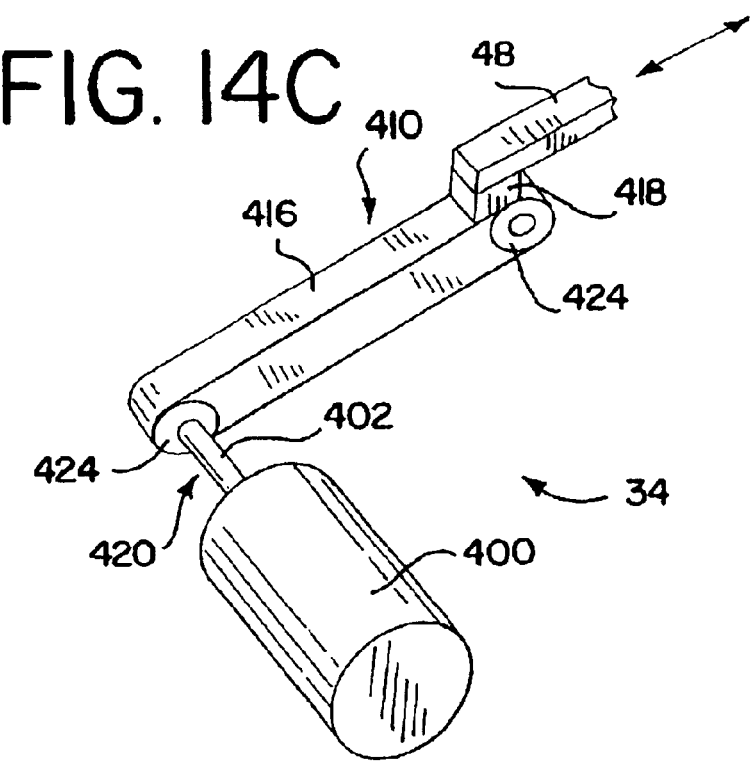
FIG. 14C is a perspective view of the component parts of the disk drive mechanism of the blood glucose sensor dispensing instrument of FIG. 1, according to one embodiment.
Figure 15:
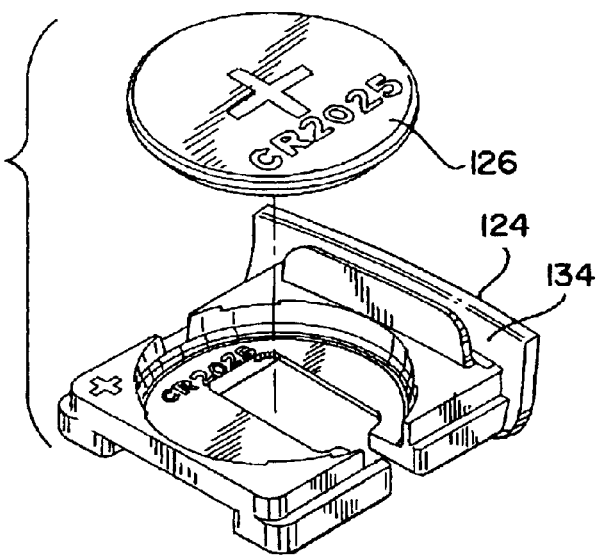
FIG. 15 is an exploded perspective view of the component parts of the battery tray sub-assembly of the blood glucose sensor dispensing instrument of FIG. 1.

As best seen in FIGS. 13, 14A, 14B, and 14C the motor 400, the linear drive system 410, and the power transfer system 420 allow the disk drive mechanism 34 to automatically load a sensor 302 into a testing position on the front end 14 of the housing 12 once the button 32 is pressed, as described below. Preferably, the motor 400 is an electrical motor, such as a DC motor, however, the motor 400 may be any device known to those skilled in the art which can provide either linear or rotational movement. The motor 400 is activated once the button 32 is pressed. Button 32 is electronically connected with motor 400 and may be placed anywhere on the housing 12. A control unit (not shown) controls the speed and direction of the motor 400. The motor 400 provides rotational movement by rotating a shaft 402, as illustrated in FIGS. 14B and 14C. Preferably, the control unit (not shown) controls the speed and direction of the shaft 402. The motor 400 is attached to the power transfer system 420 (as viewed in FIGS. 14B and 14C). In one embodiment the shaft 402 of the motor 400 is connected with the power transfer system 420. The power transfer system 420 is connected with the motor 400 and the linear drive system 410. The power transfer system 420 transfers the power provided by the motor to the linear drive system 410 and translates the linear or rotational movement provided by the motor 400 into linear movement for the linear drive system, as illustrated in FIGS. 14B and 14C. The power transfer system also steps the power of the motor up by slowing down the rotational speed through a series of gears The linear drive system 410 is connected with the disk drive mechanism 34 and the power transfer system 420, wherein the linear drive system 410 moves the disk drive mechanism 34 when the motor 400 is activated. Preferably, the linear drive system 410 is connected with the pusher 48 of the disk drive mechanism 34 and moves the pusher 48 when the motor 400 is activated.

In one embodiment, the power transfer system 420 includes at least one gear 422 for transferring power and translating movement from the motor 400 to the linear drive system 410, as illustrated in FIG. 14B. Preferably, a series of gears 422 are used to transfer power and translate movement from the motor 400 to the linear drive system 410, as illustrated in FIG. 14B. The linear drive system 410 includes a lead screw 412 and a nut 414 threaded on the lead screw 412, wherein the nut 414 is connected with and moves the disk drive pusher 48 as the lead screw 412 is rotated. In one embodiment, the lead screw 412 is a double helix screw, which allows the lead screw and the motor to rotate in only one direction instead of two, in order to move the disk drive pusher 48 from the standby position to the extended position, and from the extended position to the testing position. The lead screw is connected to the gears 422 through a lead screw connector 426, as illustrated in FIG. 14B. Preferably, at least one gear 422 is connected with shaft 402, while a second gear 422 is connected with the lead screw connector 426, as illustrated in FIG. 14B.

In one embodiment, the power transfer system 420 includes at least one roller 424 for transferring power and translating movement from the motor 400 to the linear drive system 410, as illustrated in FIG. 14C. The roller 424 is connected with the shaft 402. The linear drive system 410 includes a belt 416 and a connecting member 418 connected to the belt. The belt 416 is wrapped around the roller 424, as illustrated in FIG. 14C. As the motor 400 is activated, the roller 424 rotates, causing the belt 416 to move. The connecting member 418 is connected with the disk drive pusher 48. Therefore, as the belt 416 moves, the disk drive pusher 48 moves as well.

An indexing disk 30 is rotatably secured to the disk drive mechanism 34 by a retainer disk 206 connected through the indexing disk 30 and into guide block 182. As best seen in FIG. 14A, the retainer disk 206 has a pair of latch arms 208 that extend through a central hole 210 in the indexing disk 30 and latch into an opening 212 in the guide block 182. As mentioned above, the indexing disk 30 includes a plurality of pins 44 protruding from the lower surface 214A thereof. These pins 44 are configured to engage notches 324 on the sensor pack 300 (see FIG. 4) so as to align and rotate the sensor pack 300 in accordance with the position of the indexing disk 30. Hence, the pins 44 and the notches 324 have the dual purpose of retaining the sensor pack 300 on the indexing disk 30 so that the sensor pack 300 will rotate with the indexing disk 30 and of positioning the sensor pack 300 in proper circumferential alignment relative to the indexing disk 30.

As previously indicated, the disk drive pusher 48 is moved towards the rear end 16 of the housing 12 (away from the testing end 14A) by motor 400 when the button 32 is pressed. The disk drive pusher 48 is guided in a lateral direction by the guide block 182, the housing guide 186, and the cover mechanism 188, as the pusher 48 is moved towards the rear end 22 of the upper case 18. As the disk drive pusher 48 slides towards the rear end 22 on the upper case 18, the indexing disk drive arm 50 causes the indexing disk 30 to rotate.

The indexing disk drive arm 50 extends rearwardly from the disk drive pusher 48. The indexing disk drive arm 50 includes a plate spring 54 made of spring type material such as stainless steel so as to bias the arm 50 outwardly from the disk drive pusher 48. A cam button 52 is affixed to the distal end of the arm 50, and is configured to engage the upper surface 216 (as viewed in FIG. 13) of the indexing disk 30. In particular, the indexing disk drive arm 50 is bent so as to protrude downwardly through a slot 218 in the guide block 182 such that the cam button 52 projects outwardly from the surface thereof. The slot 218 is designed such that the indexing disk drive arm 50 and the cam button 52 can move along the slot 218 as the disk drive pusher 48 is moved back and forth during the testing procedure. The slot 218 also prevents the indexing disk drive arm 50 from moving sideways with respect to the disk drive pusher 48 (i.e., it provides lateral support to the indexing disk drive arm 50).

As best seen in FIG. 13, the upper surface 216 of the indexing disk 30 comprises a series of radially extending grooves 60 and a plurality of curvilinearly extending grooves 56. The cam button 52 is configured to ride along these grooves 56 and 60 during the movement of the disk drive pusher 48. As the disk drive pusher 48 slides towards the rear end 22 of the upper case 18, the cam button 52 moves along one of the curvilinearly extending grooves 56. This causes the indexing disk 30 to rotate. In the preferred embodiment shown, there are ten radially extending grooves 60 and ten curvilinearly extending grooves 56 equally spaced about the circumference of the indexing disk 30, with each radially extending groove 60 being disposed between a pair of curvilinearly extending grooves 56. Accordingly, the movement of the disk drive pusher 48 towards the rear end 22 on the upper case 18 results in a $\frac{1}{10}^{th}$ rotation of the indexing disk 30.

As the button 32 is pressed, and the pusher 48 is moved towards the rear end 16 of the housing 12, the cam button 52 passes over an outer step 220 that separates the outer end 222 of the curvilinearly extending groove 56 from the adjacent radially extending groove 60. The outer step 220 is formed by the difference in depth between the outer end 222 of the curvilinearly extending groove 56 and the outer end 224 of the adjacent radially extending groove 60. In particular, the outer end 224 of the radially extending groove 60 is deeper than the outer end 222 of the curvilinearly extending groove 56. Thus, when the cam button 52 moves from the curvilinearly extending groove 56 into the adjacent radially extending groove 60, the biasing force of the plate spring 54 of the indexing disk drive arm 50 causes the cam button 52 to travel downwardly past the outer step 220. The outer step 220 prevents the cam button 52 from re-entering the outer end 222 of the curvilinearly extending groove 56 when the direction of travel of the disk drive pusher 48 is reversed (as will be explained below).

Rotation of the indexing disk 30 causes the sensor pack 300 to likewise rotate so that the next available sensor cavity 304 is placed in a standby position adjacent to the testing end 14A of the housing 12. The sensor pack 300 rotates with the indexing disk 30 because of the engagement of the notches 324 on the sensor pack 300 by the pins 44 on the indexing disk 30. As explained above, each sensor cavity 304 contains a disposable sensor 302 that is used during the glucose testing procedure.

Further rearward movement of the disk drive pusher 48 is prevented by a rear wall 226 on the guide block 182. In the preferred embodiment shown, the rear wall 226 includes a slotted housing 180 for holding the elastomeric connector 174 that connects the electronics assembly 62 to the flex circuit 156 disposed in the lower case 24. An interior edge 228 of the disk drive pusher 48 engages the rear wall 226 on the guide block 182 when the disk drive pusher 48 is in the fully extended position (see FIG. 6).

Upon reaching the rear end 16 of the housing 12, the pusher 48 then changes direction and moves inwardly back past the standby position (FIG. 1) and into a testing position (FIG. 7). As previously indicated, the inward movement of the pusher 48 causes the disk drive mechanism 34 to remove a sensor 302 from the sensor pack 300 and place the sensor 302 into a testing position.

As best seen in FIGS. 13 and 14A, the disk drive mechanism 34 includes a knife blade assembly 58 that is pivotally mounted to the disk drive pusher 48. The knife blade assembly 58 comprises a swing arm 230 having a first end 232 that is pivotally connected to the disk drive pusher 48 by a pair of pivot pins 234. A knife blade 36 is connected to the second end 236 of the swing arm 230. The second end 236 of the swing arm 230 also includes a first cam follower 238 and a second cam follower 240, each in the shape of a transversely extending post. The first cam follower 238 is configured to follow a pathway formed on one side of the knife blade assembly 58 by the guide block 182, the housing guide 186, and the cover mechanism 188. In particular, this pathway is formed by a cam projection 242 on the housing guide 186 that forms an upper pathway 244 between the cam projection 242 and the cover mechanism 188 and a lower pathway 246 between the cam projection 242 and the guide block 182. When the first cam follower 238 is disposed in the upper pathway 244, the knife blade 36 is in the retracted position. On the other hand, when the first cam follower 238 is disposed in the lower pathway 246, then the knife blade 36 is in the extended position. The upper pathway 244 and the lower pathway 246 are connected together at both ends of the cam projection 242 so as to form a continuous loop about which the first cam follower 238 can travel.

The second cam follower 240 engages a cam spring 248 attached to the housing guide 186. As will be explained below, the cam spring 248 guides the knife blade assembly 58 from the lower pathway 246 to the upper pathway 244 when the disk drive pusher 48 is initially moved rearward from standby position towards the extended position. The disk drive pusher 48 also comprises a spring 250 for biasing the knife blade 36 towards the extended position when the disk drive pusher 48 is initially moved forward from the extended position towards the testing position. In the preferred embodiment shown, the spring 250 comprises a plate spring that presses against the upper side of the swing arm 230.

As the button 32 is pressed, the disk drive pusher 48 is moved laterally towards the testing or front end 14 of the housing 12. As the disk drive pusher 48 begins to move forward, the spring 250 biases the swing arm 230 downwardly towards the indexing disk 30 so that the first cam follower 238 engages a sloped surface 252 on the interior end 268 of the cam projection 242 and is forced into the lower pathway 246. This causes the knife blade 36 to assume an extended position whereby the knife blade 36 projects outwardly through a knife slot 46 in the indexing disk 30 to pierce the protective foil 310 covering one of the sensor cavities 304 and engage the notch 312 on the back end 308 of the sensor 302 contained therein. As the disk drive pusher 48 continues to move towards the front end 20 of the upper case 18, the first cam follower 238 continues along the lower pathway 246, thereby causing the knife blade 36 to remain in the extended position projecting through the knife slot 46 so that it will travel along the knife slot 46 and push the sensor 302 forward out of the sensor cavity 304 and into a testing position at the front end 14 of the housing 12. The sensor 302 is in the testing position when the front end 306 of the sensor 302 projects out of the sensor opening 254 formed on the front end of the guide block 182. While in the testing position, the sensor 302 is prevented from being pushed back through the sensor opening 254 by the engagement of the knife blade 36 against the notch 312 on the back end 308 of the sensor 302.

As the disk drive pusher 48 reaches the testing position, the front end 204 of the disk drive pusher 48 simultaneously engages the sensor actuator 40 and the button release 66. In particular, the front end 204 of the disk drive pusher 48 engages and pushes the button release 66 outwardly so as to project upwardly from the upper surface of the upper case 18. At the same time, the front end 204 of the disk drive pusher 48 engages a contact pad 256 on the sensor actuator 40 so as to force the sensor actuator 40 downward. This downward motion causes a pair of metal contacts 38 on the sensor actuator 40 to project into the sensor opening 254 on the guide block 182 and engage the contacts 314 on the sensor 302 for the glucose testing procedure. The metal contacts 38 also apply a frictional force to the sensor 302 so that the sensor 302 does not prematurely fall out of the sensor opening 254 prior to completion of the glucose testing procedure. In the preferred embodiment shown, the metal contacts 38 are somewhat flexible and are made of stainless steel. The housing guide 186 includes support ribs 187 disposed adjacent to the metal contacts 38 so as to prevent the metal contacts 38 from bending. As explained above, the metal contacts 38 permit the transmission of electrical signals between the sensor 302 and the electronics assembly 62 during the glucose testing procedure.

When the glucose testing procedure is completed, the button release 66 is depressed to release the sensor 302 from the testing position. The linear drive system 410 then moves the disk drive pusher 48 towards the front end 14 of the upper case 18 even more causing the sensor 302 to be pushed forward out of the sensor opening 254 so that the sensor 302 is free from the instrument 10 and can be disposed.

As mentioned above, when the disk drive pusher 48 is pushed from the extended position towards the testing position, the cam button 52 on the indexing disk drive arm 50 travels along one of the radially extending grooves 60 to prevent the indexing disk 30 and the sensor pack 300 from rotating. The radially extending groove 60 includes a sloped portion 260 that changes the depth of the groove 60. In particular, the sloped portion 260 decreases the depth of the radially extending groove 60 so that the middle portion of the radially extending groove 60 is shallower than the curvilinearly extending grooves 56. The radially extending groove 60 also comprises an inner step 262 near its inner end 264 (i.e., near the center of the indexing disk 30). The inner step 262 is formed along the juncture of the inner end 264 of the radially extending groove 60 and the inner end 266 of the curvilinearly extending groove 56. As the disk drive pusher 48 is pushed from the extended position towards the testing position, the cam button 52 travels up the sloped portion 260 of the radially extending groove 60, past the inner step 262, and into the adjacent curvilinearly extending groove 56. The biasing force of the plate spring 54 of the indexing disk drive arm 50 causes the cam button 52 to travel downwardly past the inner step 262. The inner step 262 prevents the cam button 52 from re-entering the radially extending groove 60 when the direction of travel of the disk drive pusher 48 is reversed (as explained above in connection with the outward movement of the disk drive pusher 48).

As the disk drive pusher 48 reaches the testing position, the first cam follower 238 passes the exterior end 270 of the cam projection 242. At the same time, the second cam follower 240 passes over the end of the cam spring 248, which retracts upwardly and out of the way as the first cam follower 238 nears the exterior end 270 of the cam projection 242. Once the first cam follower 238 has passed the end of the cam spring 248, the cam spring 248 moves downwardly so as to engage and guide the second cam follower 240 upwardly when the direction of travel of the disk drive pusher 48 is reversed and pulled outward towards the extended position. In particular, when the disk drive pusher 48 is subsequently moved into the extended position, the cam spring 248 guides the second cam follower 240 upwardly so that the first cam follower 238 enters the upper pathway 244 and the knife blade 36 is retracted.

As explained above, the disk drive pusher 48 is moved outwardly to initiate the testing procedure. During the outward motion of the disk drive pusher 48, the cam button 52 on the indexing disk drive arm 50 travels along one of the curvilinearly extending grooves 56 so as to rotate the indexing disk 30. During this outward motion, the first cam follower 238 on the knife blade assembly 58 travels along the upper pathway 244. As a result, the knife blade 36 is retracted from the knife slot 46 on the indexing disk 30 so that the indexing disk 30 is free to rotate in response to action of the cam button 52 in the curvilinearly extending groove 56. As the disk drive pusher 48 reaches the fully extended position, the first cam follower 238 passes the interior end 268 of the cam projection 242 and is guided into the lower pathway 246 by the biasing force of the spring 250 on the swing arm 230 of the knife blade assembly 58.

Prior to operating the sensor dispensing instrument 10, a sensor pack 300 must first be loaded into the sensor dispensing instrument 10 if one has not already been so loaded, or if all of the sensors 302 in the previously loaded sensor pack 300 have been used. To load a sensor pack 300, the lower case 24 and the upper case 18 are opened by depressing the latch 72 on the lower case 24. In the preferred embodiment shown, the opening of the lower case 24 and the upper case 18 causes the elastomeric connector 174 to separate from the contacts 166 on the autocal disk 158, thereby breaking the electrical connection between the autocal disk 158 and the electronics assembly 62. This causes an electronic counter (which is part of the electronics assembly 62) that keeps count of the number of unused sensors 302 in the sensor pack 300 to re-set to zero (0).

The opened housing 12 is then turned so that the lower surface 214 of the indexing disk 30 faces upwardly as shown in FIG. 3. A sensor pack 300 is then placed on the indexing disk 30 by aligning the notches 324 along the periphery of the sensor pack 300 with the pins 44 on the indexing disk 30. The lower case 24 is then pivoted on to the upper case 18 so as to enclose the sensor pack 300 within the housing. Once the lower case 24 is secured to the upper case 18 by the latch 72, the sensor dispensing instrument 10 is ready for operation.

The following is a brief description of the operation of the sensor dispensing instrument 10. First, the button 32 is pressed which causes the sensor dispensing instrument 10 to turn ON and the cam button 52 on the indexing disk drive arm 50 to travel along one of the curvilinearly extending grooves 56 on the upper surface 216 of the indexing disk 30 so as to rotate the indexing disk 30 $\frac{1}{10}^{th}$ of a complete rotation. The rotation of the indexing disk 30 causes the sensor pack 300 to be rotated so that the next one of the sensor cavities 304 is placed in a standby position aligned with the testing end 14 of the housing 12. At the same time, the knife blade assembly 58 is retracted and moved towards the center of the indexing disk 30.

Next, the pusher 48 moves away from the rear end 16 of the housing 12 causing the knife blade assembly 58 is pivoted downwardly so that a knife blade 36 pierces a portion of the protective foil 310 covering the sensor cavity 304 in the standby position and engages the sensor 302 in the sensor cavity 304. As the pusher 48 continues to move away from the rear end 16 of the housing 12, the knife blade assembly 58 forces the sensor 302 out of the sensor cavity 304 and into a testing position at the front end 14 of the housing 12. At the same time, the cam button 52 on the indexing disk drive arm 50 travels along one of the radially extending grooves 60 to prevent the indexing disk 30 from rotating.

After the sensor 302 has been completely ejected from the sensor cavity 304 and pushed into a testing position projecting out from the front end 14 of the housing 12, the sensor actuator 40 engages the sensor 302 to hold the sensor 302 in the testing position and to couple the sensor 302 to the electronics assembly 62. The front end 306 of the sensor is then inserted into a drop of blood to be tested, whereby the blood is analyzed by the electronics assembly 62. The results of the analysis are then displayed on the liquid crystal display 64 of the sensor dispensing instrument 10.

Once the analysis of the blood is complete, the linear drive system 410 then moves the disk drive pusher 48 towards the front end 14 of the upper case 18 even more causing the sensor 302 to be pushed forward out of the sensor opening 254 so that the sensor 302 is free from the instrument 10 and can be disposed. The linear drive system 410 then returns the knife blade 36 to the standby position.

While the invention has been described with reference to details of the illustrated embodiment, these details are not intended to limit the scope of the invention as defined in the appended claims. For example, the sensor dispensing instrument 10 can be used for testing fluids other than blood glucose. In fact, the sensor dispensing instrument 10 can be used in connection with the analysis of any type of chemistry fluid that can be analyzed by means of a reagent material.

What is claimed is:

1. A sensor dispensing instrument adapted to handle a sensor pack containing a plurality of sensors, each of said plurality of sensors being disposed in a sensor cavity on said sensor pack and enclosed by a protective covering, said sensor dispensing instrument further adapted to perform a test using one of said plurality of sensors, and comprising:
    an outer housing having a front end and a rear end, said outer housing further comprising a sensor opening through which one of said sensors is disposed to conduct the test, said sensor opening being disposed at the front end of the outer housing;
    a motor generally disposed within the outer housing;
    a linear drive system generally disposed within the outer housing;
    a power transfer system connected with the motor and the linear drive system for transferring power from the motor to the linear drive system;
    a disk drive mechanism generally disposed within the outer housing and connected to the linear drive system, the disk drive mechanism including a disk drive pusher, wherein the linear drive system moves the disk drive pusher when the motor is activated.

2. The sensor dispensing instrument according to claim 1, wherein the a disk drive mechanism further includes an indexing disk for supporting and rotating said sensor pack, an indexing disk drive arm for rotating said indexing disk, a knife blade assembly for puncturing said foil covering and ejecting one of said sensors from said sensor cavity and through said sensor opening, wherein said indexing disk drive arm and said knife blade assembly are mounted on said disk drive pusher.

3. The sensor dispensing instrument according to claim 1, wherein said sensor dispensing instrument is operated by engaging the motor to move the disk drive pusher in a first direction so as to cause said indexing disk drive arm to rotate said indexing disk, and move the disk drive pusher in a second direction so as to cause said knife blade assembly to puncture the foil covering and eject one of said sensors from said sensor cavity and through said sensor opening.

4. The sensor dispensing instrument according to claim 1, wherein a button is affixed to the outer housing, and further wherein said button is pressed to electronically engage said motor and cause said motor to move the disk drive pusher.

5. The sensor dispensing instrument according to claim 1, wherein the linear drive system includes a lead screw and a nut on the lead screw, wherein the nut is connected with and moves the disk drive pusher as the lead screw is rotated.

6. The sensor dispensing instrument according to claim 5, wherein the lead screw is a double-helix screw.

7. The sensor dispensing instrument according to claim 1, wherein the linear drive system includes a belt and a connecting member connected with the belt, wherein the connecting member is connected with and moves the disk drive pusher as the belt is rotated.

8. The sensor dispensing instrument according to claim 1, wherein the power transfer system includes at least one gear for transferring power from the motor to the linear drive system.

9. The sensor dispensing instrument according to claim 1, wherein the power transfer system includes a roller for transferring power from the motor to the linear drive system.

10. A sensor dispensing instrument adapted to handle a sensor pack containing a plurality of sensors, comprising:
    an outer housing comprising a sensor opening;
    a motor generally disposed within the outer housing;
    a linear drive system generally disposed within the outer housing;
    a power transfer system connected with the motor and the linear drive system, wherein the power transfer system transfers power from the motor to the linear drive system; and
    a disk drive mechanism generally disposed within the outer housing and connected with the linear drive system, wherein a sensor is disposed through said sensor opening when said motor is activated.

11. The sensor dispensing instrument according to claim 10, wherein the disk drive mechanism includes an indexing disk for supporting and rotating said sensor pack, an indexing disk drive arm for rotating said indexing disk, a knife blade assembly for puncturing said foil covering and ejecting one of said sensors from said sensor cavity and through said sensor opening, and a disk drive pusher on which said indexing disk drive arm and said knife blade assembly are mounted, said disk drive pusher being movable with respect to said outer housing.

12. The sensor dispensing instrument according to claim 11, wherein said sensor dispensing instrument is operated by activating the motor so as to cause said indexing disk drive arm to rotate said indexing disk, and so as to cause said knife blade assembly to puncture the foil covering and eject one of said sensors from said sensor cavity and through said sensor opening.

13. The sensor dispensing instrument according to claim 10, wherein the linear drive system includes a lead screw and a nut on the lead screw, wherein the nut is connected with and moves the disk drive mechanism as the lead screw is rotated.

14. The sensor dispensing instrument according to claim 10, wherein the power transfer system includes at least one gear.

15. The sensor dispensing instrument according to claim 10, wherein the sensor dispensing instrument is adapted to perform a test by using a fluid testing sensor, wherein said fluid testing sensor is being supplied by a disposable sensor pack inserted into said sensor dispensing instrument, wherein said sensor pack has a plurality of sensor cavities covered by a protective covering, and wherein said fluid testing sensor is enclosed in one of said sensor cavities prior to the performance of said test.

* * * * *